US006977251B2

(12) United States Patent
Loria

(10) Patent No.: US 6,977,251 B2
(45) Date of Patent: Dec. 20, 2005

(54) 5-ANDROSTENE-3β, 17α DIOL AS AN INHIBITOR OF TUMOR GROWTH

(76) Inventor: Roger M. Loria, 3219 Brook Rd, Richmond, VA (US) 23227-4803

( * ) Notice: Subject to any disclaimer, the term of this patent is extended or adjusted under 35 U.S.C. 154(b) by 34 days.

(21) Appl. No.: 09/225,499

(22) Filed: Jan. 6, 1999

(65) Prior Publication Data

US 2001/0014675 A1 Aug. 16, 2001

Related U.S. Application Data

(63) Continuation of application No. 08/838,823, filed on Apr. 10, 1997.

(51) Int. Cl.$^7$ .............................................. A61K 31/56
(52) U.S. Cl. ...................................................... 514/182
(58) Field of Search ........................................ 514/182

(56) References Cited

U.S. PATENT DOCUMENTS

| | | | | |
|---|---|---|---|---|
| 2,521,586 | A | * | 9/1950 | Levy et al. ................. 514/182 |
| 2,845,381 | A | * | 7/1958 | Tindall ....................... 514/182 |
| 3,963,707 | A | | 6/1976 | Högberg et al. |
| 4,628,052 | A | | 12/1986 | Peat |
| 4,652,553 | A | | 3/1987 | Hagmann et al. |
| 4,652,637 | A | | 3/1987 | Hagmann et al. |
| 4,835,147 | A | | 5/1989 | Roberts |
| 4,898,694 | A | | 2/1990 | Schwartz et al. |
| 4,942,154 | A | | 7/1990 | Durette et al. |
| 5,001,119 | A | | 3/1991 | Schwartz et al. |
| 5,028,631 | A | | 7/1991 | Schwartz et al. |
| 5,206,008 | A | | 4/1993 | Loria |
| 5,461,042 | A | | 10/1995 | Loria |
| 5,478,566 | A | | 12/1995 | Loria |
| 5,744,462 | A | | 4/1998 | Schwartz et al. |
| 5,837,269 | A | | 11/1998 | Daynes et al. |
| 5,843,932 | A | | 12/1998 | Labrie |
| 5,912,240 | A | | 6/1999 | Loria |
| 6,407,079 | B1 | | 6/2002 | Müller et al. |
| 6,642,227 | B2 | | 11/2003 | Cao et al. |
| 2003/0181434 | A1 | | 9/2003 | Loria |

FOREIGN PATENT DOCUMENTS

WO   WO 02/072003      9/2002

OTHER PUBLICATIONS

Carter et al., Chemotherapy of Cancer, Second Edition, 1981, John Wiley & Sons, N.Y., N.Y., pp. 362–365.*
Begue et al, "C$_{19}$ Steroides Urinaires Dans Une Luteose Ovarienne Gravidique" *Journal of Steroid Biochemistry* vol. 8, pp. 737–742 (1977) (English Summary).
Von Lubos Starka et al, "Biogenese von Freiem und Sulfatiertem 7α–Hydroxy–Androstenolon in Zellfraktionen der Rattenleber", *Hoppe–Seyler's Z. Physiol. Chem.* Bd. 348, S.293–302 (Mar. 1967) (English Summary).

Bjorkhem et al., "Metabolism of Steroids in Germfree and Conventional Rats Treated with a 3β–Hydroxy–Δ$^5$–Steroid Oxidoreductase Inhibitor", *Eur. J. Biochem.* vol. 16, pp. 557–566 (1970).
DeFaye et al., "Microbiologicl 7–and 15–Hydroxylations of C–19 Steroids", *Journal of Steroid Biochemistry*, vol. 9, pp. 331–336 (1978).
Adams, J.B., et al., "Enzymic synthesis of steroid sulfates. XIV. Properties of human adrenal steroid alcohol sulfotransferase", *Biochim. Biophys. Acta* 664(3), 460–8 (1981).
Adams, John, et al., "Adrenal dehydroepiandrosterone and human mammary cancer", *Cancer Res.* 38 (11, Pt.2), 4036–40 (1978).
Dehennin, L., et al., "Long–term administration of testosterone enanthate to normal men: Alterations of the urinary profile of androgen metabolites potentially useful for detection of testosterone misuse in sport", *J. Steroid Biochem. Mol. Biol.* 44(2), 179–89 (1993).
Huynh, P., et al., "Contrasting effects of alpha– and beta–andrestenediol on oncogenic myeloid cell lines in vitro", *Journal of Leukocyte Biology*, vol. 62, pp. 258–267 (1997).
Kohara, H., et al., "Stereospecific removal of the 16 alpha–hydrogen in the biosynthesis of 5, 16–androstadien–3 beta–ol from pregnenolone," *Biochimica et Biophysica Acta*, vol. 921, pp. 90–95 (1987).
Mancuso, S., et al., "Amniotic 5–androstene–3 beta, 17 alpha–diol in high risk pregnancy", *J. Steroid Biochem.*, 95–6 (1980).
Plotz, E., et al., "Enzymic activities related to steroidogenesis in postmenopausal ovaries of patients with and without endometrial carcinoma", *Am. J. Obstet. Gynecol.* 99(2), 182–97 (1967).
Ruokonen, A., et al., "Free and sulfate–conjugated neutral steroids in human testis tissue", *Biochemistry*, 12(8) 1411–16 (1972).
Rozhin, J., et al., "Endcrine steroid sulfotransferases: Steroid alcohol sulfotransferase from human breast carcinoma cell line MCF–7," *J. Steroid Biochem.*, vol. 25, No. 6, pp. 973–979 (1986).
Huhtaniemi, I., et al., "Ultrastructural and steroidogenic characteristics of an androgen–producing andrenocortical tumour," *Clinical Endrocrinology*, vol. 8, pp. 305–314 (1978).
Kwan, T., et al., "Gas chromatographic–mass spectrometric study of metabolites of $C_{21}$ and $C_{19}$ steroids in neonatal porcine testicular microsomes," *Biochem. J.*, vol. 227, pp. 909–916 (1985).

(Continued)

*Primary Examiner*—Rebecca Cook

(57) ABSTRACT

The instant application provides means of accelerating cell aging and programed cell death in tumor cells by administration of 3β,17α androstenediol (αAED) or its ethers or esters.

9 Claims, No Drawings

OTHER PUBLICATIONS

Huf, P., et al., "The in vitro biosynthesis of epitestosterone and testosterone from $C_{19}$ steroid precursors in the testis of the lizard *tiliqua rugosa*," *General and Comparative Endrocrinology*, vol. 75, pp. 280–286 (1989).

Rozhin et al., "Endrocine Steroid Sulfotransferases: Steroid Alcohol Sulfotransferase From Human Breat Carcinoma Cell Line MCF–7," *Steroid Biochem.*, 1986, pp. 973–979, vol. 25, No. 6.

Pasqualini, "Role of Androgens in Breast Cancer," *J. Steroid Biochem. Molec. Biol.*, 1993, pp. 167–172, vol. 45, Nos. 1–3.

Segaloff, A., "Testosterone and Miscellaneous Steroids in the Treatment of Advanced Mammary Cancer," *Cancer*, vol. 10, pp. 808–812 (1957).

Chang, H., et al, "Suppression of $\Delta^5$–androstenediol–induced androgen receptor transactivation by selective steroids in human prostate cancer cells", *PNAS*, vol. 96, pp. 11173–11177, Sep., 1999.

Gustafsson, J., et al, "Steroids in urine from a patient with adrenocortical carcinoma after treatment with op'-DDD", Steroidologia, 2, pp. 27–37, (1971).

Huynh, P., et al., "17 Alpha androstenediol inhibition of breast tumor cell proliferation in estrogen receptor–positive and—negative cell lines", *Cancer Detection and Prevention*, 24(5), pp. 435–444, (2000).

Miyamoto, H., et al, "$\Delta^5$–Androstenediol is a natural hormone with androgenic activity in human prostate cancer cells", *PNAS*, vol. 95, pp. 11083–11088, (Sep. 1998).

Oertel, G., et al, "The effects of steroids on glucose–6–phosphate dehydrogenase", *J. Steroid of Biochemistry*, vol. 3, pp. 493–496, (1972).

Ruzicka, L., et al, "Sex hormones XIII. Concerning cis–t-estosterone and other 17–cis–hydroxy derivatives of androstane and androstene", Helv Chim. Acta 19, pp. 842–845, (1936) (translation from German).

Segaloff, A., et al., "Hormonal therapy in cancer of the breast. II. Effect of methylandrostenediol on clinical course and hormonal excretion", *Cancer*, vol. 5(2), pp. 271–274, (Mar. 1952).

Segaloff, A., et al, "Hormonal therapy in cancer of the breast. XI. The effect of dehydroepiandrosterone on clinical course and hormonal excretion", *Cancer*, vol. 10(6), pp. 1114–1115, (1957).

Adams, J.B., et al. Enzymic synthesis of steroid sulfates. XII. Isolation of dehydroepiandrosterone sulfotransferase from human adrenals by affinity chromatography, *BIochimica or Biophysica Acta* 567(1) 144–153 1979.

Axelson, M., et al. Changes in the metabolic profile of steroids in urine during ethanol metabolism in man , *Journal of Steroid Biochemistry* 14(2):155–159 1981.

Ruzicka, L. et al. Sex hormones XIII Preparation of 17–ethyl–testosterone and the 3–trans, 17–cis–diols of androstane and androstane Further contributions on the specificity of the sex hormones, *Helv Chim. Acta* 19:357–365 1936 (translated from German).

Segaloff, A., et al, Hormonal therapy in cancer of the breast. IV. Effect of androstenediol on clinical course and hormonal excretion *Cancer*, 5(6):1179–1181 1952.

* cited by examiner

5-ANDROSTENE-3β, 17α DIOL AS AN INHIBITOR OF TUMOR GROWTH

This application is a continuation of U.S. Ser. No. 08/838,823 filed Apr. 10, 1997, now pending.

BACKGROUND OF THE INVENTION

1. Field of the Invention

This invention relates to the field of pharmaceuticals for tumor-inhibitory effects. The 5-androstene 3β,17α diol (αAED), its esters and ethers, are taught herein to achieve tumor-inhibiting effect.

2. Description of Related Art

Mifepristone (RU486) is used as a progesterone receptor antagonist (See U.S. Pat. No. 4,386,085, which is incorporated herein by reference in its entirety) and has been shown to have use both as an abortifacient and has been found useful for treating steroid-dependent breast cancer.

Flutamide, which has been disclosed in U.S. Pat. No. 3,847,988 (which is incorporated herein by reference in its entirety) is an antiandrogen that has been used to treat prostatic cancer, usually in conjunction with estrogen.

U.S. Pat. No. 2,521,586 to Levy, et al., teaches production of the 17-monobenzoate ester of androstene diol. No use of the 5-androstene 3β,17α diol (αAED) is taught therein.

Peat, in U.S. Pat. No. 4,628,052 teaches a genus which might, arguably, within the scope of the genus, encompass the αAED. However, all examples and all named compounds require a keto group. Hence, it is reasonable to conclude that the αAED is not intended therein.

Tindall, in U.S. Pat. No. 2,845,381 teaches cosmetic compositions containing the αAED. No medicinal compositions appropriate for internal use or medicinal uses are suggested therein.

U.S. Pat. No. 4,882,322 to Johnson, et al. Teaches substituted 5-androstene 3β,17β diol to regulate or inhibit the conversion of androgens to estrogens. The αAED is not taught therein.

Swartz, et al., in U.S. Pat. No. 4,898,694 teaches a very large group of compounds which encompass substituted androstenediols. However, Schwartz does not suggest the αAED nor the esters and ethers claimed herein for any purpose.

Loria, in U.S. Pat. Nos. 5,206,008, 5,277,907, 5,3876, 583, 5,461,042 and 5,478,566 teaches that the 5-androstene 3β,17β diol (βAED) and 5,-androstene 3β,7β,17β triol (AET) enhance immune response, and also are useful for counteracting the untoward effects of irradiation and chemotherapy, and buffer the anti-proliferative effects of hydrocortisone. None of these patents teaches or suggests use of αAED. As taught therein, the βAED is most effective if administered in such a manner that it contacts tissue of ectodermal origin.

SUMMARY OF THE INVENTION

The instant invention provides a means of accelerating cell aging and programmed cell death in tumor cells. The practice of the invention involves administration of 3β,17α androstenetriol (which may be referred to in this application as either 17αAED or simply αAED) and esters and ethers thereof.

DESCRIPTION OF THE INVENTION

The instant invention relates to the use of 5-androstene 3β,17α diol (herein referred to as αAED or 17 αAED), its esters and ethers, to inhibit growth and accelerate cell aging, induce apoptosis and death of tumor cells as a means of treating malignancies. The active agents of the invention may also be used as contraceptives and abortifacients. The active agents are of the structure:

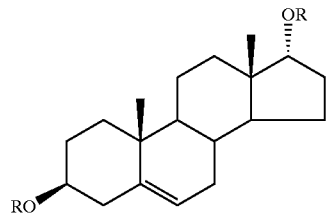

wherein R may be H, alkenyl of 2–8 carbons, alkyl of 1–8 carbons, phenylalkyl of 1–4 carbons, phenyl or $COR_2$, wherein $R_2$ is H; alkyl of 1–8 carbons, alkenyl of 2–8 carbons, phenylalkyl wherein the alkyl has 1–4 carbons (including benzyl) or phenyl. Any phenyl moiety may have up to three substituents chosen from among hydroxy, carboxy of 1–4 carbons, halo, alkoxy of 1–4 carbons, alkyl of 1–4 carbons, or alkenyl of 2–4 carbons and wherein any alkyl may be a straight chain, branched chain, or the alkyl may be wholly or partially cyclized.

It has been found that these active agents, when administered as described herein, inhibit cell growth. The αAED is administered in sufficient dosages to provide a blood concentration of from 5 to 10,000 ηM when given systemically. A more preferred blood or tissue fluid concentration is in the rang of 10 to 10,000 ηM. The dosage will vary with the type of cell to be inhibited. The method of administration will depend on the location of the target cells. Such means as parenteral or oral administration are also appropriate. The αAED may also be administered by applicator or in a spray to tissue during surgery. Compositions containing the active agents taught herein may be administered vaginally or rectally either by instillation of a liquid composition or on supports such as sponges.

Other preferred methods of administration include buccal, sublingual, nasal or endotracheal routes. Sprays or mists may be useful for such administration. Furthermore, sprays may be useful for administration to the operative area during surgery. For example, sprays may be used to contact the peritoneal cavity or the thoracic cavity during surgery.

Compositions of the invention may also be administered to the intestinal mucosa by oral or rectal routes. Suppositories, solutions for use as retention enemas and creams or jellies are appropriate means for use in rectal administration.

Compositions of the invention may also be applied to the vaginal mucosa using creams, jellies suppositories or douching solutions. The compositions may be in the form of prophylactic vaginal preparations or may be used in lubricants on condoms. Jellies and creams may also be administered by application in a cervical diaphragm which, when in place, will provide for prolonged contact with the cervix.

For purposes of administration into an orifice of the body, the compositions of the invention may be administered via a flexible tube into the target site. As indicated previously, the compositions containing αAED may be administered as a douche or retention enema. Other target sites include the bladder, uterus, trachea, nasopharynx, sinus or (via the nasal passage) the pituitary.

The carrier system used in a given instance will depend on the mode of administration. The active agents are lipophilic compounds. Solvents and carriers for lipophilic steroids known in the art are appropriate for use in the compositions containing αAED or the esters and ethers of αAED. Examples of such carriers are glycols such as polypropylene glycol, polyethylene glycol, ethanol, DMSO and cyclodextrins (especially the amorphous cyclodextrins). Cyclodextrins will pass through the buccal mucosa into the circulation easily. This method is particularly appropriate for administration as a means of avoiding intravenous administration while bypassing the liver. Other vehicles that should be considered include fatty acid esters of polyoxyethylene sorbitol (Tweens) or sorbitan (Spans) for preparation of emulsions.

The compositions taught herein may be used to treat most neoplasms, including for, for example, use in treatment of neoplasms, including those of the blood-forming organs, the liver, pancreas, thyroid, andrenals, pituitary, ovaries, testicles, breast, central nervous system (including brain, spinal column), bone, connective tissue, lungs, liver, the gastro-intestinal system, uterus, mucous membranes, mouth and tongue, the lining of the peritoneum, the lymphatics and sensory organs.

Materials and Methods:

The βAED, 17 beta-oestradiol and tamoxifen were obtained from Sigma Chemical Company (St. Louis, Mo.). The αAED and Flutamide were obtained from Steraloid, Inc. (Walton, N.H.) and Schering Corporation (Kenilworth, N.J.), respectively. All steroids except βAED were dissolved in ethanol. βAED was dissolved in DMSO:ETHOL (1:1 v/v). Stock solutions were filtered and kept at 4° C. For testing, stock solutions were diluted in media immediately before use. The final concentration of vehicle was always $\leq 0.2\%$ in all samples, and this concentration had no significant cytotoxic effect on the human breast cell cancer cell line designated ZR-75-1 (American Type Culture Collection) as determined by trypan blue exclusion.

The ZR-75-1 cell line (passage 89) was obtained from the American Type Culture Collection (Rockville, Md.). The cells were cultured in RPMI-1640 medium containing 10% heat-inactivated fetal calf serum, 200 $\mu$M L-glutamine, 10 NM HEPES, 1.5 U/ml penicillin, and 1.5 $\mu$g/ml streptomycin in 5% $CO_2$ at 37° C. The cells were passaged twice weekly.

Cell Growth for testing:

Cells were first seeded at initial density of $1 \times 10^5$ cells per ml in quadruplicates in 24 multi-well flat bottom plates (Costar). Cells were then allowed to adhere and grow in phenol red-free RPMI 64 media supplemented with 10% heat-inactivated fetal calf serum (FCS), 200 $\mu$M L-glutamine, 10 mM HEPES, 2.5 U/ml penicillin and 2.5 $\mu$g/ml streptomycin in 5% $CO_2$ at 37° C. After 48 hours, four wells were sacrificed and counted to determine plating efficiency. In the remaining wells, medium was removed by aspiration and cells in each well were exposed to the media containing the specified steroid. The controls containing only medium or medium with vehicle were also prepared. In all samples, medium was changed every 48 hours. At the pre-established time-point. Cells were removed by trypsinization and washed. Cell number and viability were determined by trypan blue exclusion using a hemocytometer. Parallel cultures were also run to determine cell proliferation.

Cell Proliferation Assays:

For cell proliferation assays, cell suspensions were prepared by trypsinization of cells from cultures prepared in accord with methods described above. Cell viability was determined by trypan blue exclusion. The cells were then seeded in flat-bottom 96-well microtiter plates at a density of $2 \times 10^3$ cells/well and were allowed to rest for 48 hours in order to adhere. Non-adherent dead cells were removed by aspiration. Cells were then grown in media without phenol red. Some of the media contained supplements as indicated above. The active agents or vehicle control were added to the media. The cells were then grown for six days. Media was changed on the samples every 48 hours. On day 6, cells were pulsed with 1 $\mu$Ci[$^3$J]-thymidine for the last 6 hours of incubation before harvesting onto glass filter using a HPD cell harvester (Cambridge Technology, Watertown, Mass.) and counted on a KLB scintillation counter.

Initial tests were carried out to determine the optimal (maximal) dose of αAED required to inhibit growth of the ZR-75-1 cells in in vitro as determined by tritiated tymidine incorporation. At concentration of 12.5 $\eta$M or greater, the αAED significantly inhibited the growth of ZR-75-1 cells, and this anti-proliferative effect occurred in a dose and time-dependent manner at half-maximal (50 $\eta$M) and maximal dose (100 $\eta$M) levels. To ensure that inhibition was not due to cytotoxicity, cell count and viability were assessed by trypan blue exclusion. The addition of the 17αAED was not toxic to the cells. As opposed to αAED, the βAED (an epimere) alone at 100 $\eta$M concentrations did not have any antiproliferative effect on the growth of the ZR-75-1 cells.

EXAMPLE 1

ZR-75-1 cells ($2 \times 10^3$) were treated as described above over a six day period with differing concentrations of αAED or with vehicle-only cultures. The medium was changed every 48 hours. Cells were pulsed with $^3$H-thymidine for the last six hours of incubation.

Results showed increasing proliferation at 6.25 $\eta$M with decreasing cell proliferation at 12.5 $\eta$M and marked decrease at concentrations of 50 $\eta$M concentrations.

EXAMPLE 2

Cells were treated as in Example 1, except that in some samples a combination of 17αAED and βAED were used. The concentration of the αAED varied while the concentration of the βAED in the samples containing the combination of agents remained constant at 2.5 $\eta$M. Cells were pulsed with $^3$H-thymidine for the last six hours.

The proliferation of cells in cultures containing αAED in the presence of βAED showed decreased proliferation at all concentrations of αAED.

EXAMPLE 3

Effects of αAED on growth of ZR-75-1 cells in the presence of estradiol was studied. Cells treated with increasing concentration of αAED in the presence or absence of 1 $\eta$M concentration of estradiol over a 6 day period were studied. Cells were treated with increasing concentration of αAED in the presence of 1 $\eta$M concentration of estradiol over a 6 day period, with medium changed every 48 hours. Cells were pulsed with $^3$H-thymidine for the last six hours of incubation. At higher doses of αAED the αAED suppressed proliferation even in the presence of estradiol. Hence, estradiol can not effectively overcome the antiproliferative activity of αAED on this human breast cancer cell line. (This indicates that αAED may be useful in prevention of estrogen-dependent breast cancer.

EXAMPLE 4

Effects of αAED on growth of ZR-75-1 cells in the presence of Flutamide, an antiandrogen, were studied using the process of Example 3 except that estradiol was replaced with Flutamide. The administration of αAED with antiandrogens, especially in treating estrogen-dependent malignancies such as breast cancer, should be considered particularly advantageous treatment option.

EXAMPLE 5

Example 5 was again studied in the presence of RU486. Again, it was shown that at effective concentrations it was possible to lower dosage of RU486 in the presence of effective amounts of 0.1 µl concentrations of αAED with 0.5 µM concentration of RU486 there was synergistic action to decrease proliferation of cells. This synergism was shown to be even greater at RU486 concentrations of 1 µM. This combination of active agents would be especially useful for treatment of tumors which are dependent on estrogen or progesterone.

EXAMPLE 6

| Preparation for instillation: | |
|---|---|
| Ingredient | % w/w |
| αAED | 0.01% |
| polypropylene glycol | 13.0% |
| Water | 86.5% |

EXAMPLE 7

| Preparation for intravenous injection: | |
|---|---|
| Ingredient | Amount |
| αAED | 1 mg. |
| Ethanol | 5 ml. |
| Phosphate buffered saline | Add to 1000 ml. |

EXAMPLE 8

Effect of αAED on growth of lymphoid neoplasm (P388D1 cells obtained from the American Type Culture Collection) in the presence of RU486 at concentration of 0.5 µM and 1.0 µM was studied in accord with the methods described above. It was found that the use of αAED in combination with RU486 resulted in increased effectiveness over use of one agent.

EXAMPLE 9

Effects of αAED at doses of 50 ηM and 100 ηM doses on murine macrophage myeloma cells (RAW 264.7, obtained from the American Type Culture Collection) was studied. At both 50 ηM and 100 ηM levels there was significant inhibition of proliferation.

EXAMPLE 10

| Preparation for instillation into the bladder for treatment of bladder cancer: | |
|---|---|
| Ingredient | Amount |
| αAED | 10 mg |
| DMSO | 100 ml |
| half-normal saline | 900 ml. |

EXAMPLE 11

Water, 100 ml, is mixed with 7 g. β-hydroxypropyl cyclodextrin and 1 mg αAED. Fill ampules with the solution and sterilize. This preparation may be added to solutions for administration to the mucosa, for oral administration, or for parenteral administration.

EXAMPLE 12

The cyclodextrin/αAED preparation is prepared as above. The material is freeze-dried and placed in sterile ampules. The resulting powder may be placed in vials. The contents of the vials may then be snorted into the nasal cavity. It is also appropriate to dissolve the contents of the vials and place in solution for intravenous or topical application, including for infusion into a wound site. It may also be applied by spraying or sponging into the operative site such as the abdominal or thoracic cavity.

EXAMPLE 13

The preparation of Example 12 is diluted with 100 ml water. The preparation is sprayed into the abdominal cavity during and after removal of a colon malignancy.

αAED may be delivered to or through the skin by any means, including subcutaneous or intradermal injection or topical application. One means of topical application is the use of skin patches impregnated with the active agent. This means of delivery is advantageous since it is non-invasive and easily administered by relatively unskilled care providers.

EXAMPLE 14

Capsules of a formulation of αAED for oral administration is prepared by mixing 2 mg. αAED, 15 mg. Starch and 5 mg. Magnesium stearate. The capsules are administered twice a day to achieve a daily dosage of 1–50 mg./da.

The compositions of the invention may be administered intrathecally either at the spinal level or into the cisterna magna.

When αAED, its esters or ethers are administered orally, it is necessary that the active agents be protected from destruction and absorption in the upper gastro-intestinal tract. The active agents are most effective when the period of exposure to the mucosa of the intestinal tract is increased. Hence use of capsules containing the active agents in formulations that effect slow release in the intestine are appropriate.

The active agents may also be used in veterinary medicine for treatment of animals suffering from tumors. For purposes of such treatment, the αAED may be added to the chow of the animals.

The sterile solutions may be administered to the lung either by bronchioscopic means or by mist which may be under pressure.

Patched for administration of αAED may be formulated as adhesive patches containing the active agent. For example, the patch may be a discoid in which a pressure-sensitive silicone adhesive matrix containing the active agent may be covered with a non-permeable backing. The discoid may either contain the active agent in the adhesive or may be attached to a support made of material such as polyurethane foam or gauze that will hold the active agent. When patches are used in treating animals, the area must be shaved or plucked. In all instances, the area to which the patch is applied should be cleaned carefully before application.

EXAMPLE 15

A patch composed of trilaminate of an adhesive matrix sandwiched between a non-permeable backing and a protective covering layer is prepared in the following manner:

To a pressure-sensitive silicone adhesive composition BIOPSA™ q7-2920 (Dow Corning Corporation, Midland, Mich., U.S.A.) In cyclohexane (50% w/v) is added sufficient αAED to provide a 0.5% αAED composition. The adhesive is applied to a polyester film to provide in successive layers about 2 mg. Of active agent per cm². Patches should be covered with a protective layer which will be removed before application.

Patches may be prepared containing permeation enhancers such as cyclodextrin, butylated hydroxyanisole, or butylated hydroxytoluene.

The active agents may be administered to the mucosa of oral, pharyngeal or nasal cavity by tablet or lozenge.

The antiproliferative agents taught herein may be used in conjunction with other active agents such as vinca alkaloids, nucleic acid inhibitors, platinum agents, interleukin-2, interferons, alkylating agents, antimetabolites, corticosteroids, DNA intercalating agents, anthracyclines and ureas. Examples of specific agents, in addition to those exemplified herein, include hydroxyurea, 5-fluorouracil, anthramycin, asparaginase, bleomycin, dactinomycin, dacabazine, cytarabine, busulfan, thiotepa, lomustine, mechlorehamine, cyclophosphamide, melphalan, mechlorethamine, chlorambucil, carmustine, 6-thioguanine, methotrexate, etc.

What I claim is:

1. A composition of matter comprising a carrier and a tumor inhibiting effective amount of a compound selected from the group consisting of 5-androstene-3β,17α-diol and an ester or ether thereof of the formula:

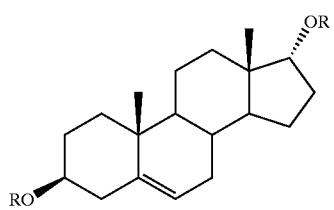

wherein,

R independently are H, alkenyl of 2–8 carbons, alkyl of 1–8 carbons, phenylalkyl of 1–4 carbons, phenyl or $COR_2$, $R_2$ independently are H, alkyl of 1–8 carbons, alkenyl of 2–8 carbons, phenylalkyl wherein the alkyl has 1–4 carbons or phenyl, wherein any phenyl moiety optionally has up to three substituents chosen from among hydroxy, carboxy of 1–4 carbons, halo, alkoxy of 1–4 carbons, alkyl of 1–4 carbons, or alkenyl of 2–4 carbons and wherein any alkyl optionally is a straight chain, branched chain, or the alkyl optionally is wholly or partially cyclized, wherein the composition is a formulation for oral, parenteral, buccal, sublingual, endotracheal or aerosol administration.

2. The composition of claim 1 wherein the compound is 5-androstene-3β,17α-diol.

3. The composition of claim 1 in the form of a tablet.

4. The composition of claim 1 in the form of a capsule.

5. A composition of matter comprising a cyclodextrin and a tumor inhibiting effective amount of a compound selected from the group consisting of 5-androstene-3β,17α-diol and an ester or ether thereof of the formula:

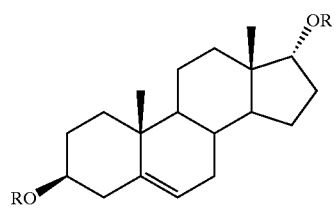

wherein,

R are selected from H, alkenyl of 2–8 carbons, alkyl of 1–8 carbons, phenylalkyl of 1–4 carbons, phenyl or $COR_2$, $R_2$ are selected from H, alkyl of 1–8 carbons, alkenyl of 2–8 carbons, phenylalkyl wherein the alkyl has 1–4 carbons or phenyl, wherein any phenyl moiety optionally has up to three substituents chosen from among hydroxy, carboxy of 1–4 carbons, halo, alkoxy of 1–4 carbons, alkyl of 1–4 carbons, or alkenyl of 2–4 carbons and wherein any alkyl optionally is a straight chain, branched chain, or the alkyl optionally is wholly or partially cyclized, wherein said composition is a formulation for oral, parenteral, buccal, sublingual, endotracheal or aerosol administration.

6. The composition of claim 5 wherein the compound is 5-androstene-3β,17α-diol.

7. The composition of claim 5 in the form of a tablet or a capsule.

8. The composition of claim 5 in the form of a parenteral formulation.

9. The composition of claim 5, wherein said composition is in a form selected from the group consisting of a spray, a cream, a jelly, a suppository, a douching solution, a liquid and an adhesive patch.

* * * * *